United States Patent [19]

Theodoropulos

[11] Patent Number: 5,294,717
[45] Date of Patent: Mar. 15, 1994

[54] BIFUNCTIONAL CHELATING AGENTS, THEIR CHELATES AND PROCESS OF PREPARATION

[76] Inventor: Spyros Theodoropulos, 2964 Hickory St., Yorktown Heights, N.Y. 10598

[21] Appl. No.: 782,061

[22] Filed: Oct. 24, 1991

[51] Int. Cl.$^5$ .................. C07D 215/22; C07D 215/24
[52] U.S. Cl. ..................................... 546/156; 546/10; 546/168; 546/169
[58] Field of Search ........................ 546/168, 169, 156; 514/311, 314

Primary Examiner—David B. Springer
Attorney, Agent, or Firm—William R. Moran

[57] ABSTRACT

Bifunctional chelating agents based on substituted 8-hydroxy-2-carboxamidoquinolines and their chelates are provided together with processes for their preparation. The agents can react with a variety of biological substrates and/or chelate with a variety of transition metals providing useflu in vivo agents for localizing radioactivity where needed for diagnostic or therapeutic purposes.

7 Claims, No Drawings

BIFUNCTIONAL CHELATING AGENTS, THEIR CHELATES AND PROCESS OF PREPARATION

FIELD OF THE INVENTION

This invention relates to novel bifunctional chelating agents based on extended 8-substituted-2-carboxamidoquinolines, useful in radioisotopic labeling of organic substrates. The chelating agents of the invention have the ability to react with compounds of biological or clinical interest to form derivatives which will chelate suitable radionuclides, resulting in radioisotopic labeling of the compounds. The 8-hydroxy-2-carboxamidoquinoline chelates of the invention are particularly useful as in vivo agents, and for localizing radioactivity, where needed, for diagnostic or therapeutic purpose.

BACKGROUND OF THE RELATED ART

It is known that chelating agents such as ethylenediaminetetraacetic acid dianhydride (EDTA-dianhydride) or diethylenetriaminepentaacetic acid dianhydride (DTPA dianhydride) can be directly coupled to biological substrates to form conjugates which can be labeled with radionuclides used in in vivo imaging applications. However, EDTA and DTPA conjugates have shown limitations as to the variety of radionuclides that can be chelated, and as to their in vivo stabilities.

Accordingly, one or more of the following objects will be achieved by the practice of the present invention. It is an object of this invention to provide 8-hydroxyquinoline derivatives which are capable of forming chelates with a variety of radionuclides. Another object of this invention is to provide bifunctional 8-hydroxyquinoline derivatives which can be readily coupled to biological substrates, and the conjugates so formed can then be labeled with radionuclides which are suitable for diagnosis and therapy. It is a further object of the invention to provide radioisotope labeled compounds possessing superior in vivo stabilities.

SUMMARY OF THE INVENTION

In its broad aspect, this invention is directed to bifunctional chelating agents characterized by the structural formula:

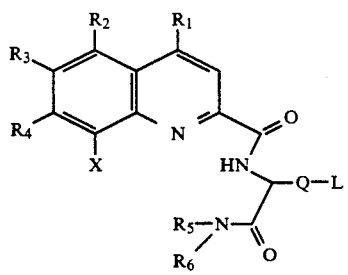

wherein X is OH or SH, and wherein $R_1$, $R_2$, $R_3$ and $R_4$ are identical or different, and are selected from the group consisting of hydrogen, hydroxyl, halogen, $C_1-C_5$ alkyl, nitro, nitroso, sulfate, sulfonate, phosphate, $C_1-C_{18}$ aryl, and heteroaryl; $R_5$ and $R_6$ are identical or different, and are selected from the group consisting of hydrogen, a $C_1-C_{18}$ alkyl group which may be substituted, such as, for example, 3-mercaptopropyl, 2-mercaptoethyl, 3-mercapto-1-carboxypropyl, 2-mercapto-1-carboxyethyl, 2-mercapto-2,2-dimethyl-1-carboxyethyl, 3-carboxypropyl, 2-carboxyethyl, carboxymethyl, 3-hydroxypropyl, 2-hydroxyethyl, 3-dimethylaminopropyl, 2-dimethylaminoethyl, and the like, or a $C_1-C_{18}$ aryl group which may be substituted, such as, for instance, phenyl, carboxyphenyl, nitrophenyl which can be reduced to aminophenyl, mercaptophenyl, naphthyl and the like, or a $C_1-C_{18}$ heteroaryl group, which may be substituted, such as hydroxypyridyl, carboxypyridyl, 8-quinolyl, and the like; wherein Q-L constitutes a group which can also be a substrate coupling moiety; wherein Q is a $C_1-C_{18}$ alkyl radical, saturated or unsaturated, and which can be substituted; it can be $C_1-C_{18}$ aryl, aralkyl, heteroaryl, heteroaralkyl, or hydrogen. When Q is hydrogen, L is non-existent; wherein L is an amine, or any group derived from an amine, such as: isothiocyanate, isocyanate, diazonium, semicarbazide, thiosemicarbazide, maleimide, haloacetamide, azide, vinylsulfonamide and halotriazineamino; wherein L can be a nitro group which can be reduced to amine, carboxyl, ester, hydroxy, sulfate, sulfonate, vinylsulfone, hydrazino, phosphate, or hydrogen. The term alkyl is C-1 to C-18 alkyl radical, saturated or unsaturated, which may be substituted; the term aryl is meant to include aromatic groups from up to 18 carbon atoms, and which may be substituted. Heteroaryl is meant to be aromatic which contains one or more of heteroatoms such as oxygen, nitrogen, sulfur, phosphorus, selenium and silicon.

The bifunctional 2-carboxamidoquinolines of the invention contain, in addition to the chelating groups, a moiety which allows for the coupling of the chelating agent to organic compounds of interest The resulting conjugates can then be readily chelated with radionuclides; the resultant radiolabeled conjugates can be used to localize radioactivity in specific organs in vivo, for diagnostic or therapeutic applications.

DETAILED DESCRIPTION OF THE INVENTION

The present invention relates to bifunctional chelating agents based on 2-carboxamidoquinolines. Each of these comprises a chelating group and a substrate reactive group including a substrate reactive moiety. Such bifunctional compounds, which may be conveniently bound to organic substrates of clinical interest, such as antibodies, other proteins, drugs, and the like, are particularly useful for in vivo diagnostic and therapeutic purposes. The 2-carboxamidoquinolines of the present invention have the formula:

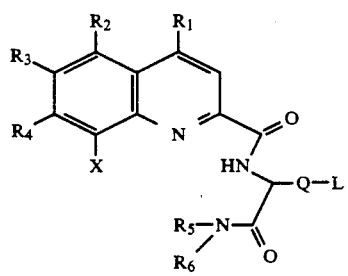

wherein X is OH or SH, and wherein $R_1$, $R_2$, $R_3$ and $R_4$ are identical or different, and are selected from the group consisting of hydrogen, hydroxyl, halogen, $C_1-C_5$ alkyl, nitro, nitroso, sulfate, sulfonate, phosphate, $C_1-C_{18}$ aryl, and heteroaryl; $R_5$ and $R_6$ are identical or different, and are selected from the group consisting of hydrogen, a $C_1$-$C_{18}$ alkyl group which may be substituted, such as, for example, 3-mercaptopropyl, 2-mercaptoethyl, 3-mercapto-1-carboxypropyl, 2-mercapto-1-carboxyethyl, 2-mercapto-2,2-dimethyl-1-carboxyethyl, 3-carboxypropyl, 2-carboxyethyl, carboxymethyl, 3-hydroxypropyl, 2-hydroxyethyl, 3-dimethylaminopropyl, 2-dimethylaminoethyl, and the like, or a $C_1$-$C_{18}$ aryl group which may be substituted, such as, for instance, phenol, carboxyphenol, nitrophenyl which can be reduced to aminophenyl, mercaptophenyl, naphthol and the like, or a $C_1$-$C_{18}$ heteroaryl group, which may be substituted, such as hydroxypyridyl, carboxypyridyl, 8-quinolyl, and the like; wherein Q-L constitutes a group which can also be a substrate coupling moiety; wherein Q is a $C_1$-$C_{18}$ alkyl radical, saturated or unsaturated, and which can be substituted; it can be $C_1$-$C_{18}$ aryl, aralkyl, heteroaryl, heteroaralkyl, or hydrogen. When Q is hydrogen, L is non-existent; wherein L is an amine, or any group derived from an amine, such as: isothiocyanate, isocyanate, diazonium, semicarbazide, thiosemicarbazide, maleimide, haloacetamide, azide, vinylsulfonamide and halotriazineamino; wherein L can be a nitro group which can be reduced to amine, carboxyl, ester, hydroxy, sulfate, sulfonate, vinylsulfone, hydrazino, phosphate, or hydrogen. The term alkyl is C-1 to C-18 alkyl radical, saturated or unsaturated, which may be substituted; the term aryl is meant to include aromatic groups from up to 18 carbon atoms, and which may be substituted Heteroaryl is meant to be aromatic which contains one or more of heteroatoms such as oxygen, nitrogen, sulfur, phosphorus, selenium and silicon The bifunctional 2-carboxamidoquinolines of the present invention were synthesized using conventional techniques, and employing either readily available materials or reagents specially designed for this purpose. A preferred method for preparing the compounds of the invention is to react an alpha amino acid of the formula I with succinimidyl 8-hydroxyquinoline-2-carboxylate of the formula II as shown below:

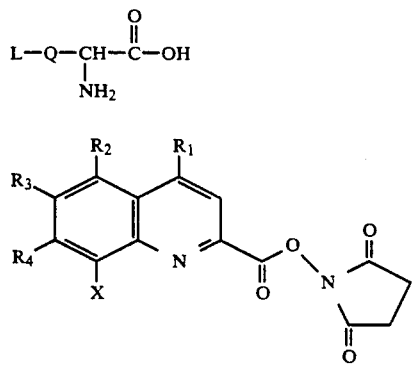

wherein Q-L, $R_1$, $R_2$, $R_3$ and $R_4$ are as indicated above. This reaction affords the 8-hydroxy-2-carboxyamidoquinoline of the formula III.

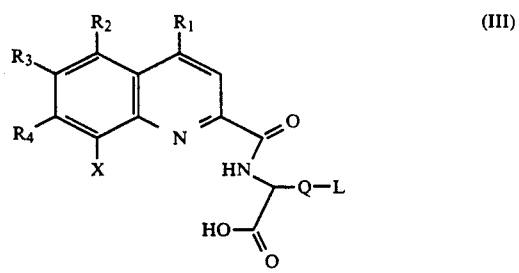

An example of an amino acid of the formula I is omega-N-(t-BOC)-lysine, and an example of a 8-hydroxyquinoline-2-carboxylate of the formula II is succinimidyl 4,8-dihydroxyquinoline-2-carboxylate. Examples 1,2 and 8 describe the synthesis of various 8-hydroxy-2-carboxamidoquinolines of the formula III.

A sequential reaction involves the 8-hydroxy-2-carboxamidoquinoline (III) and a second alpha amino acid containing a beta or a gamma mercapto group of the formula IV:

$$R_5\text{—NH—}R_{66} \qquad (IV)$$

wherein $R_5$ and $R_6$ are identical or different, and are as indicated above. In this reaction, the compound of the formula III is first allowed to react with N-hydroxysuccinimide in the presence of N,N'-dicyclohexylcarbodiimide to form the N-hydroxysuccinimide ester of the formula V:

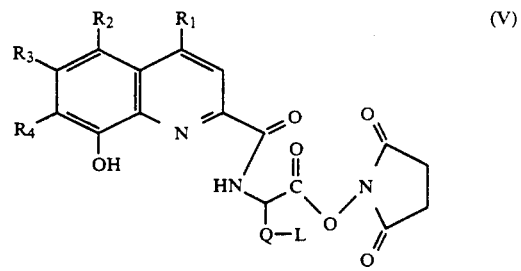

wherein Q-L, $R_1$, $R_2$, $R_3$ and $R_4$ are as described previously. The succinate ester V, made in situ, is then allowed to react with the amine IV to yield the compound of the invention whose formula is shown below:

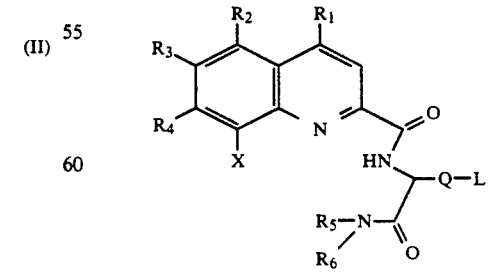

wherein Q-L, $R_1$, $R_2$, $R_3$, $R_4$, $R_5$ and $R_6$ and are as described previously. Typical examples of the amine IV are shown below.

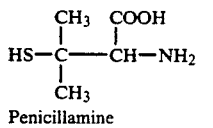
Penicillamine

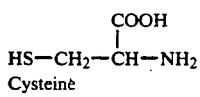
Cysteine

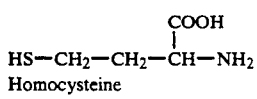
Homocysteine

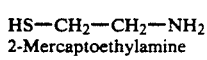
2-Mercaptoethylamine

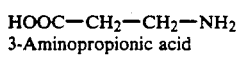
3-Aminopropionic acid

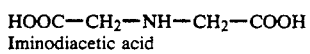
Iminodiacetic acid

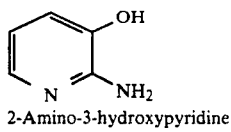
2-Amino-3-hydroxypyridine

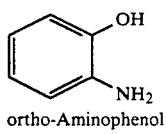
ortho-Aminophenol

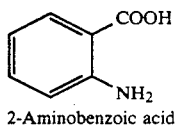
2-Aminobenzoic acid

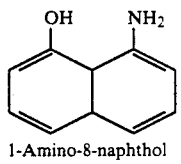
1-Amino-8-naphthol

Examples 3 to 7, 9 and 12 describe the synthesis of various compounds of the present invention.

An alternate route to the synthesis of the compounds of the present invention might first involve the coupling of the amine IV with the amino acid I to form the conjugate VI:

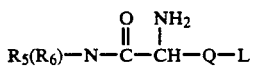

wherein Q, L, $R_5$ and $R_6$ are as shown previously. In this reaction, the amine of the amino acid I is first protected using well known techniques of peptide synthesis. Examples of protecting groups are tert-butoxycarbonyl and trifluoroacetyl moieties. The protected amino acid is then allowed to react with the amine IV to form the peptide from which the protected amino group is demasked to give VI. Example-11 describes the synthesis of a conjugate of the formula VI.

Examples of protected alpha amino acids ar shown below:

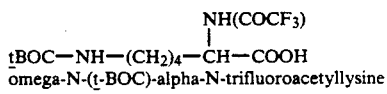
omega-N-(t-BOC)-alpha-N-trifluoroacetyllysine

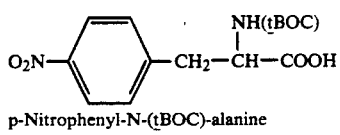
p-Nitrophenyl-N-(tBOC)-alanine

In the final step of the synthesis of the compounds of the invention, using this alternate route, an intermediate of the formula VI is reacted with 8-hydroxy-quinoline-2-carboxylic acid succinimide ester II to form the compound shown below. Q-L, $R_1$, $R_2$, $R_3$, $R_4$, $R_5$ and $R_6$ in the structure are as described previously.

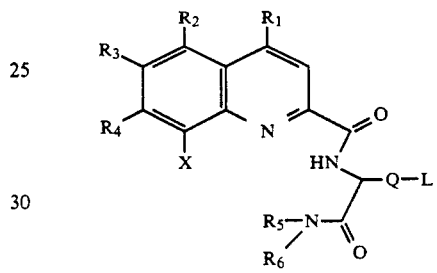

Example-12 describes the synthesis of an example of this compound using the alternate method.

The bifunctional 8-hydroxy-2-carboxamidoquinolines of the invention can be coupled to biological substrates or clinical compounds of interest, through the L group in various ways, to form adducts. For example, when the L group is a t-BOC protected amino group, the amine is first deblocked using conventional techniques, and is then either used directly for further coupling or converted to isothiocyanato, maleimido or azido groups to serve as coupling moieties using appropriate techniques known in the art. When the L group is a nitro group such as nitrophenyl, for example, the nitro group is first reduced to amine which then can serve in further couplings to biological substrates of interest. In certain cases, it is preferable to attach the biological substrate of interest to the amino acid bearing the Q-L group through the L functional moiety of the latter. The resulting conjugate can then be coupled, via its alpha amino group, to 8-hydroxyquinoline-2-carboxylic acid. An example demonstrating this route of attachment is the coupling of lysine, through its omega amino group, to biotin to form omega N-biotinyl-L-lysine. (This compound is also commercially available from SIGMA Corporation; it is offered under the name 'biocytin'.)

The adducts of the 8-hydroxy-2-carboxamidoquinolines, of this invention, and organic substrates are best represented by the formula:

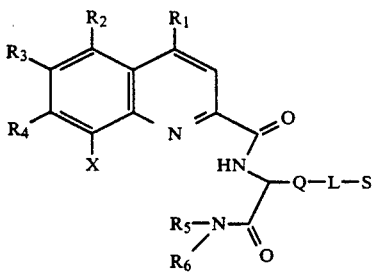

wherein $R_1$, $R_2$, $R_3$, $R_4$, $R_5$, $R_6$, Q and L are as described previously. S is a substrate of interest representing an organic molecule, drug, hormone, enzyme, antibody, peptide, polypeptide, and the like.

The 8-hydroxy-2-carboxamidoquinolines or the 8-hydroxy-2-carboxamidoquinoline adducts of this invention are receptive to chelation. The choice of the particular radionuclide will, of course, depend upon the intended use of the chelate (diagnosis or therapy) and the ability of the particular radionuclide to complex with the chelating agent. Illustrative radioisotopes are: technitium-99m, indium-111, yttrium-90, rhenium-186, holmium-166, and the like. The metal chelates of the compounds of this invention are best shown in the formula:

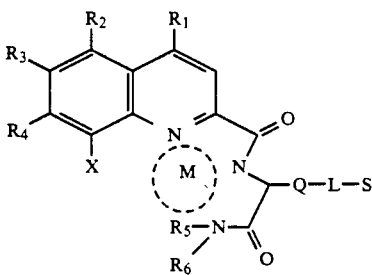

wherein Q-L, $R_1$, $R_2$, $R_3$, $R_4$, $R_5$, $R_6$ and S are as described previously; M is a transition metal ion which may also be radioactive.

As indicated previously, the compounds of the present can be chelated with metal ions by conventional procedures. In practice, the chelates are formed by reacting the quinoline derivatives with a salt of the metal ion under conditions which promote the formation of a couple between the two reactants. A wide variety of metal salts of the metal ions can be utilized in the practice of the invention. The only requirement being that the metal salt is one which will form the metal chelate with the quinoline and will not adversely effect the properties of the final chelated compound.

The choice of the particular metal ion will be dependent, of course, on the intended use of the chelate and whether such use is in vivo or in vitro, as well as the ability of the particular metal ion to form the chelate compound with the quinoline derivative.

Suitable ions, include but are not limited to, transition metal ions which are radioactive or paramagnetic and include radioactive metal ions such as, technetium-99m, indium-111, ytrium-90, gallium-67, osmium-67, cesium-137, and the like, and paramagnetic metal ions, such as, gondolinium, ferric ions, manganese, copper, and the like. Thus for example, technetium-99m is preferred for radioisotopic imaging while ytrium-90 is preferred for radioisotopic therapy. Gondolinium is the preferred paramagnetic metal ion for use in nuclear magnetic resonance.

In practice, the chelates are formed by reacting the quinoline derivative with a salt of a metal ion by conventional procedures and under conditions which promote the formation of a complex between the two reactants.

A wide variety of metal salts of the metals can be utilized in the practice of the present invention. The only requirement of the metal salt is that it be one which will form the metal chelate with the quinoline derivative and not adversely affect the properties of the final chelated compound Salts which can be employed include, but is not limited to the inorganic salts such as the chlorides, nitrates, sulfates and the like, and organic salts such as metal alkoxy salts, triflates and the like.

Preparation of the chelates of the quinoline derivatives and the metal ions is effected in the conventional manner for the preparation of chelation compounds. In practice, this can be accomplished by contacting the quinoline with an appropriate metal ion salt in an inert, liquid medium. As shown in the examples, the quinoline derivative and a metal salt was mixed in the an inert liquid, such as methanol, and stirred at room temperature. The quinoline derivatives of this invention being receptive to chelation, may be advantageously utilized in any of the several known techniques involving the use of radioisotopes for diagnostic or therapeutic purposes, or in imaging systems which utilize nuclear magnetic resonance.

For example, the chelates of this invention can be employed in in vivo imaging to detect tumor cells or as diagnostic agents to determine the functioning of organs in warm blooded animals including man. The particular chelate employed will be dependent upon the nature of the proposed diagnostic procedure or the intended therapeutic treatment.

The novel compounds of this invention are accordingly intended for use in a variety of systems which utilize radioisotopes or change in electronic properties of a compound such as in nuclear magnetic resonance.

As previously indicated the metals which are combined with the quinoline derivatives of the invention are the metals which exhibit radioactive or paramagnetic properties and can be used in imaging systems. The novel compounds of this invention are accordingly intended for use in the labeling of biological compounds of interest utilzing radioisotopes or paramagnetic metal ions. Furthermore the compounds of this invention are intended for use in a variety of systems which utilize the detection of radioisotopes or change in electronic properties of a compound such as in nuclear magnetic resonance.

By employing the procedures and reactants set forth above and in the following examples, the following illustrative 8-hydroxy-2-carboxamidoquinoline compounds can be prepared:

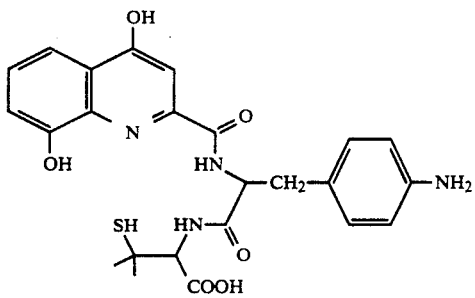
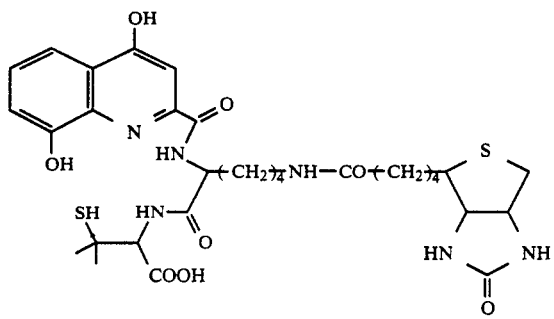
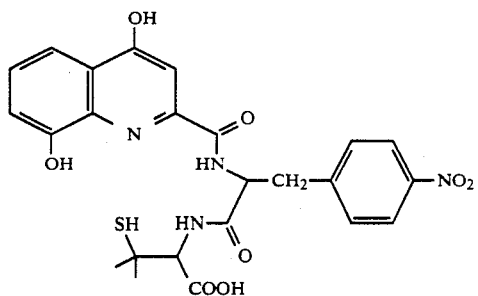
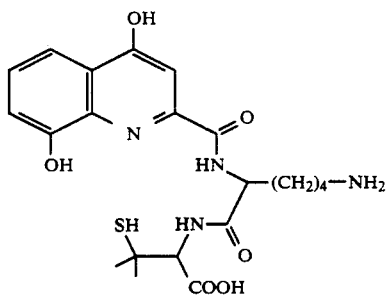
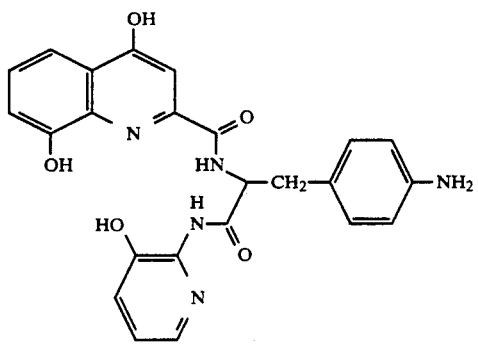

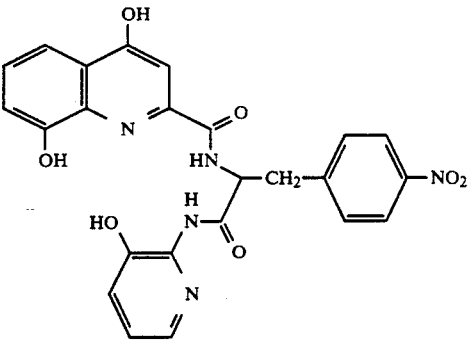

The following examples illustrate the best mode presently contemplated for the preparation of 8-hydroxy-2-carboxamidoquinolines, their adducts and the chelates.

EXAMPLE-1

4,8-Dihydroxyquinoline-2-carbonyl-N-(N-(tertbutoxycarbonyl)lysine 4,8-Dihydroxyquinoline-2-carboxylic acid (1.0 g; 4.88 mmol), dicyclohexylcarbodiimide (1.1 g; 5.37 mmol) and N-hydroxysuccinimide (0.62 g; 5.39 mmol) were combined in 10 mL of anhydrous DMF, and stirred in an argon atmosphere for 18 h. The precipitated dicyclohexyl urea was filterd off. The filtrate containing succinimidyl (4,8-dihydroxyquinoline-2carboxylate) was added dropwise to a solution of N-(tert-butoxycarbonyl)-L-lysine (1.26 g; 5.11 mmol) and potassium carbonate ( 1.7 g; 12.3 mmol) in 30 mL of water. The resultant mixture was diluted to 50 mL with water, and the yellow colloidal solution was stirred at the room temperature for 3h. The reaction mixture was quickly acidified with aqueous hydrochloric acid to pH 2, and the precipitated product was filtered off, washed with water, and dried by azeotropic removal of water. The dry yellow powder was stirred with methanol for 2h and filtered. The filtrate was concentrated on a rotary evaporator and the yellow product was dried under vacuum. Yield: 0.87 g. TLC (silica gel RP-18 precoated glass plate from MERCK, 0.25 mm thick, and with fluorescent indicator; water/acetonitrile 2:1 as developer) $R_f$ 0.28. The spot was visualized under short wavelength UV. The product was homogeneous by TLC. $^1$H NMR spectrum (200 MHz; DMSO-$d_6$+$D_2O$) showed signals at 7.69 (dbr, 1H, J=8), 7.46 (t, 1H, J=8), 7.34 (sbr, 1H), 7.18 (dbr, 1H, J=8), 4.59 (m, 1H), 2.96 (m, 2H), 1 95 (m, 2H), 1.38–1.44 (multiplets, 4H) and 1.34 (s, 9H).

EXAMPLE-2

4,8-Dihydroxyquinoline-2-carbonyl-N-(4-nitro)-DL-phenylalanine 4,8-Dihydroxyquinoline-2-carboxylic acid (1 g; 4.88 mmol) was converted to the corresponding succinimidyl ester as described in Example-1. The solution of the succinimidyl ester in dimethylformamide was added dropwwise to a stirred aqueous solution of 4-nitro-DL-phenylalanine (1.1 g; 5.24 mmol) and potassium carbonate (1.7 g; 12.3 mmol), and the reaction mixture was diluted to 50 mL of colloidal yellow solution. After 3h of reaction, acidification to pH 2, and the further processing of the precipitated product exactly as described in Example 1 yielded 1.25 g of product as yellow solid. TLC: (silica gel RP-18; water/acetonitrile 2:1 as developer) $R_f$ 0.28. The spot was visualized under short wavelength UV. The product was homogeneous by TLC. $^1$H NMR spectrum (200 MHz; DMSO-$d_6$+$D_2O$) showed signals at 7.59–8.04 (overlapping doublets, 5H), 7.46 (t, 1H, J=8.3), 7.35 (sbr, 1H), 7.23 (dd, 1H, J=1.2, 8.3), 5.08 (dd, 1H, J=5,10) and 3.50 (m, 2H).

EXAMPLE-3

4,8-Dihydroxyquinoline-2-carbonyl-N-(N-tertbutoxycarbonyl)lysylpenicillamine 4,8-Dihydroxyquinoline-2-carbonyl-N-(N -(tert-butoxycarbonyl)-L-lysine (217 mg; 0.5 mmol), obtained as in Example-1, was esterified with N-hydroxysuccinimide (63 mg; 0.55 mmol) and dicyclohexylcarbodiimide (113 mg; 0.55 mmol) in 0.8 mL of DMF, at the room temperature and in an argon atmosphere, for 18 h. The DMF solution of the corresponding succinimidyl ester, after filtering off dicyclohexyl urea, was added dropwise to a solution of D-penicillamine (82 mg;0.55 mmol) and potassium carbonate (190 mg; 1.38 mmol) in 2 mL of water, stirred in an argon atmosphere The reaction mixture was further diluted to 5 mL with water, and stirred under argon for 2h. Acidification to pH 2 followed by filtration of the precipitated material yielded 180 mg of solid, which was a 2:1 mixture of product and the starting material (by TLC analysis). This mixture was dissolved in minimum methanol and placed on a column (25 mm OD, 13 cm ht) of silicagel RP-18 (230–400 mesh; purchased from EM Separations) packed in 5:3 methanol-water system. Elution using the same solvent system and a 12 psi argon pressure led, after TLC analyses of collected fractions and combining of appropriate fractions, to the recovery of 100 mg of the product TLC: $R_f$ 0.63 (silica gel RP-18; 1:1 acetonitrile/water). The starting material has the $R_f$ of 0.75 under the same conditions. $^1$H NMR spectrum (200 MHz; DMSO-$d_6$+$D_2O$) showed signals at 7.71 (dbr, 1H, J=8.8), 7.43 (ddbr, 1H, J=8.8,7.7), 7.32 (sbr, 1H), 7.18 (dbr, 1H, J=7.7), 4.64 (d, 1H, J=4.4), 2.98 (m, 2H), 1.94 (m, 2H), 1.78 (m, 2H), 1.45 (sbr, 3H), 1.41 (sbr, 3H) and 1.33 (s, 9H).

EXAMPLE-4

4,8-Dihydroxyquinoline-2-carbonyl-N-(4-nitro)-DL-phenylalanylpenicillamine

Succinimidyl 4,8-dihydroxyquinoline-2-carbonyl-N-(4-nitro)phenylalanine was prepared from 200 mg of the precursor acid (0.5 mmol), DCC (110 mg; 0.53 mmol) and N-hydroxysuccinimide (63 mg; 0.55 mmol) in 1 mL of DMF under conditions described in the examples above. The succinimidyl ester in DMF was added to a solution of D-penicillamine (78.8 mg; 0.53 mmol) and potassium carbonate (174 mg; 1.26 mmol) in 2 mL of water, stirred in an argon atmosphere Acidification to pH 2, after 2 h of reaction, gave the product which was filtered, dissolved in minimum methanol, and subjected to flash chromatography using the conditions described in Example-3 above. This yielded 98 mg of product as pale yellow solid ($R_f$0.2 in silica gel RP-18, 1:1 acetonitrile/water system) and the recovery of 28 mg of the starting material $^1$H NMR spectrum (200 MHz; DMSO-$d_6$+$D_2O$) showed signals at 8.04 (d, 1H, J=7.4), 7.58-7.77 (unresolved multiplets, 4H), 7.45 (t, 1H, J=7.9), 7.34 (sbr, 1H), 7.19 (dbr, 1H, J=7.4), 5.20 (two dds in 1:1 ratio, 1H), 4.65 (d, 1H, J=8.5), 3.39 (m, 2H), 1.48, 1.46 & 1.43 (singlets, 6H in all). The doubling up of the multiplet at 5.20 and the methyl singlets is indicative of the presence of two diastereomers, in 1:1 ratio, arising due to the use of DL-4-nitrophenylalanine in this preparation. Apparently, the signal positions due to the rest of the protons are the same for both the isomers.

EXAMPLE-5

4,8-Dihydroxyquinoline-2-carbonyl-N-lysylpenicillamine 30 mg of the tert-butoxycarbonyl derivative of the title compound, prepared as described in Example-3, was stirred with 0.5 mL of trifluoroacetic acid at the room temperature, in an argon atmosphere, for 30 minutes. The reaction mixture was concentrated on a rotary evaporator. Traces of trifluoroacetic acid were removed by successive co-evaporation with toluene and hexane. The resultant oily material, which is the trifluoroacetate of the title compound, was homogeneous by TLC. $R_f$0.46 (silica gel RP-18; methanol/water 1:1 ). The starting material has the $R_f$ of 0.1 under the same conditions.

EXAMPLE-6

4.8-Dihydroxyquinoline-2-carbonyl-N-(4-nitro)-DL-phenylalanyl-(2-amino-3-hydroxy)pyridine The succinimidyl ester of 200 mg of 4,8- dihydroxyquinoline-2-carbonyl-N-(4-nitro)phenylalanine was prepared as described in Example-4 and reacted with 2-amino-3-hydroxypyridine (72 mg; mmol; 0.65 mmol; 1.3 equiv) at the room temperature for 18 h. Water was added and the product was extracted with diethyl ether. 250 mg of brownish material, homogeneous by TLC, was obtained $R_f$0.38 (silica gel RP-18; 1:1 acetonitrile/water). The starting material has the $R_f$ of 0.5 and 2-amino-3-hydroxypyridine has the $R_f$ of 0.07 under the same conditions. $^1$H NMR spectrum (200 MHz; DMSO-$d_6$+$D_2O$) showed signals at 7.12–8.09 (overlapping signals; 11H), 5.32 (m, 1H) and 3.50 (m, 2H).

EXAMPLE-7

4,8-Dihydroxyquinoline-2-carbonyl-N-(4-amino)-DL-phenylalanyl-(2-amino-3-hydroxy)pyridine 150 mg of the product from Example-6 above was dissolved in methanol and hydrogenated over 10% Pd/C using 30 psi hydrogen pressure over 4 h in a Parr's apparatus. The catalyst was filtered off, and the solvent was evaporated off to obtain the hydrogenated product as brown powder. $R_f$0.19 (silica gel RP-18; 2:3 acetonitrile/water). The starting material has the $R_f$ of 0.09 under the same conditions.

EXAMPLE-8

4,8-Dihydroxyquinoline-2-carbonyl-N-biocytin

Succinimidyl 4,8-dihydroxy-2-carboxylate, prepared from 44 mg (0.215 mmol) of xanthurenic acid, 48 mg (0.233 mmol) of DCC and 25 mg (0.22 mmol) of N-hydroxy-succinimide in 0.5 mL of DMF, according to procedures given in examples above, was added to a stirred solution of 80 mg (0.21 mmol) of biocytin (N-biotinyl-L-lysine; commercially available from SIGMA) and 74 mg (0.54 mmol) of potassium carbonate in 0.5 mL of water. The reaction mixture was diluted with water to 3 mL of colloidal yellow solution. After 2.5 h, acidification to pH 2 yielded a yellow solid (30 mg) which was pure by TLC criterion. More of the product was present in the filtrate, along with some unreacted starting material and N-hydroxysuccinimide.

TLC: R$_f$ 0.5 (silica gel RP-18, water/acetonitrile 2:1). The starting material has the R$_f$ of 0.67 in this system.

EXAMPLE-9

4,8-Dihydroxyquinoline-2-carbonyl-N-biocytinyl-DL-penicillamine

The DMF solution of the succinimidyl ester, prepared from 30 mg of the product from example -8, 12 mg of DCC and 7 mg of NHS in 0.3 mL of DMF, was added to a solution of 9 mg of DL-penicillamine (1.1 equiv) and 18.5 mg of potassium carbonate (2.5 equiv) in 0.3 mL of water, and the mixture was diluted to 2 mL of colloidal yellow solution. After stirring for 3 h, acidification to pH 2, followed by filtration of precipitated material gave the product as yellow solid. TLC: R$_f$ 0.38 (silica gel RP-18, water/acetonitrile 2:1). The diastereomers, arising due to the usage of DL-penicillamine, did not resolve in this solvent system.

EXAMPLE-10

4,8-Dihydroxy-5-sulfonato-quinoline-2-carboxlic acid 1.0 g of xanthurenic acid was added in portions to 3.5 mL of concentrated sulfuric acid. The clear viscous solution was stirred at 100° C. (bath temperature) for 18 h. The reaction mixture was cooled to room temperature, and 25 mL of water were carefuilly added. The brownish yellow material (1 g), which precipitated over 24 h, was filtered off, solubilized in hot 5% aqueous hydrochloric acid, and filtered. The clear yellow filtrate was set aside for 24 h. The fine yellow needles of the product (the title compound), which crystallized from the solution, was filtered and dried. Yield of the first crop: 0.39 g. Signals, in $^1$H NMR spectrum (200 MHz; DMSO-d$_6$+D$_2$O), at 7.63 (center of AB quartet, J=8.6) and 6.93 (s, 1H) were supportive of the structure.

EXAMPLE 11

(N t-butoxycarbonyl)Biocytinyl-D-penicillamine

N-(tert-butoxycarbonyl)Biocytin was prepared according to a published procedure (Ed Bayer & M. Wilcheck, *Methods in Enzymology*, 34 (20), page 266). 150 mg of this colorless solid (0.32 mmol) was converted to the corresponding succinimidyl ester using 72 mg of DCC and 40 mg of NHS in 1 mL of DMF. After 24 h, the DMF solution of the succinimide ester was added to the aqueous solution of 52 mg (1.1 equiv) of D-penicillamineand 58 mg of potassium carbonate in 5 mL of water. Solid potassium carbonate was added to adjust the pH to 8. After stirring for 3 h, the pH was adjusted to 3 using 10% aqueous citric acid. The precipitated colorless solid (90 mg) was found to be approximately 9:1 mixture of the product and the starting material (TLC criterion). TLC analysis was carried out using silica gel RP-18 coated glass plate (0.25 mm thickness) and acetonitrile/water (1:1) system for development. The products on the TLC plates were visualized as pink spots on a white background using 4-dimethylaminocinnamaldehyde spray reagent. R$_f$ 0.31 for the product, and 0.38 for the starting material. This 9:1 mixture of product and starting material was used as such for reaction with succinimidyl 4,8-dihydroxy-5-sulfonatoquinoline-2-carboxylic acid.

EXAMPLE-12

4,8-Dihydroxy-5-sulfonato-quinoline-2-carbonyl-N-biocytinylpenicillamine

This experiment involves the following three stages:

(1) 5-Sulfonatoxanthurenic acid (39.4 mg; 0.138 mmol), described in Example-10, was converted to the corresponding succinimidyl carboxylate by reacting with 31.1 mg of DCC and 17.4 mg of NHS in 0.5 mL of DMF for 18 h at the room temperature (under argon atmosphere).

(2) t-BOC-biocytinylpenicillamine (90 mg), described in Example-11, was stirred with 0.5 mL of trifluoroacetic acid (TFA) for 30 minutes. Removal of TFA led to biocytinylpenicillamine (as the TFA salt) in quantitative yield. The starting material in this reaction also had about 10% of t-BOC-biocytin, which was reflected as the corresponding demasked material (10%) in the reaction product.

(3) The succinimidyl ester (in DMF) from step-1 above was added dropwise to a stirred solution of product from step-2 above, and 86 mg of potassium carbonate in 2 mL of water. Stirring for 2 h folowed by acidification to pH 1.2 gave a clear solution which was concentrated on a rotary evaporator. The residue was extracted with toluene to remove residual DMF. The residue was redissolved in 4 mL of water, chilled in a freezer for 1 h, thawed to room temperature and filtered off to remove the precipitated 5-sulfonatoxanthurenic acid. The clear filtrate was concentrated, and the concentrate was subjected to flash chromatography, as described in Example-3, using 20% acetonitrile/water as eluent. Fractions of 8 mL size were collected after setting aside the first eluate corresponding to the dead volume. The pure product was obtained in fraction #4; the TLC of the same showed homogeneous band which was visible under UV, which also showed up as pink spot upon spraying with 4-dimethylaminocinnamaldehyde, a reagent specific for biotinylated products. Recovery: 16 mg. TLC: R$_f$ 0.26 (silica gel RP-18, 20% acetonitrile/water). 5-Sulfonatoxanthurenic acid moves to the solvent front under the same conditions.

EXAMPLE-13

Chelation of a biotinylated chelator to Tc-99m 4,8-Dihydroxyquinoline-2-carbonyl-N-biocytinylpenicillamine (described in Example-9) was chelated to technitium-99m using the following procedure. 40 uL of a commercial sample of glucoheptonate (containing tin) was mixed with 60 uL of pertechnetate (Tc-99m; generator eluate; 3 mCi) and set aside for fifteen minutes at room temperature. To 9 uL of the chelating agent sample (#19-61-1; concentration: 1 mg/mL in 1:1 DMF/1% saline mixture) was added 1 uL of 5M sodium acetate (pH=6) followed by 5 uL of glucoheptonate/pertechnetate prepared as described above. The resultant solution was left at the room temperature for 1 h. The assay was carried out by combining the biotinylated chelate with avidin, and separating the protein fraction on sephadex G-50 column using saline as eluent. Greater than 95% of radioactivity was recovered in the protein fractions, attesting to the efficiency of both labeling using trans chelation technique and binding to avidin. A control experiment using avidin presaturated with biotin gave 0% of radioactivity in the protein fractions.

What is claimed is:

1. An 8-substituted-2-carboxamidoquinoline compound having the structure:

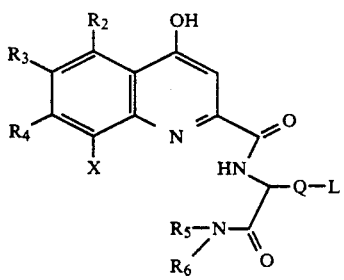

wherein:

$R_2$, $R_3$ and $R_4$ are identical or different, and are selected from the group consisting of hydrogen, hydroxyl, halogen, $C_1$-$C_5$ alkyl, nitro, nitroso, —$SO_3H$, —$PO_3H$, and an aryl up to $C_{18}$;

X is selected from the group consisting of OH and SH;

$R_5$ and $R_6$ are identical or different, and are selected from the group consisting of hydrogen, a $C_1$-$C_{18}$ alkyl group which may be unsubstituted or substituted with a member selected from the group consisting of mercapto, carboxy, hydroxy and dialkylamino; an aryl up to $C_{18}$ which may be substituted with at least one member selected from the group consisting of hydroxy, carboxy amino and mercapto groups; and a pyridyl or 8-quinolyl group which may be substituted with a member selected from the group consisting of hydroxy and carboxy;

the group Q-L represents a substrate coupling moiety, wherein Q is hydrogen, a $C_1$-$C_{18}$ alkyl group which may be unsubstituted or substituted with the same substituents as $R_5$ and $R_6$ above, an aryl and aralkyl up to $C_{18}$ pyridyl or 8-quinolyl; with the proviso that when Q is hydrogen, L is nonexistent;

L is a nitro, or an amino group.

2. A compound of the claim 1 having the chemical structure:

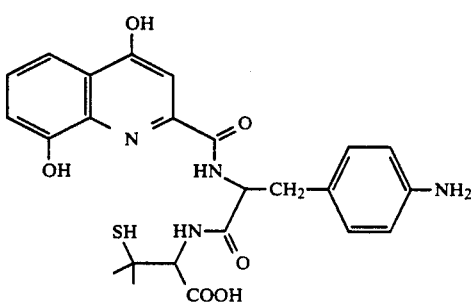

3. A compound having the chemical structure:

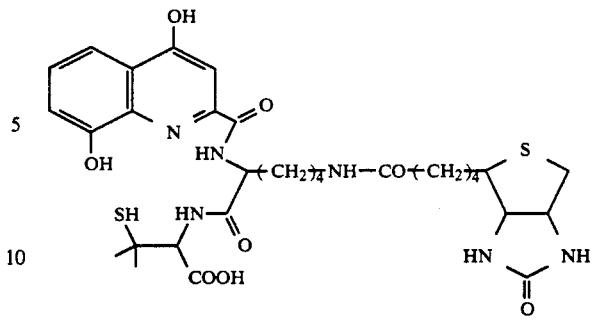

4. A compound of the claim 1 having the chemical structure

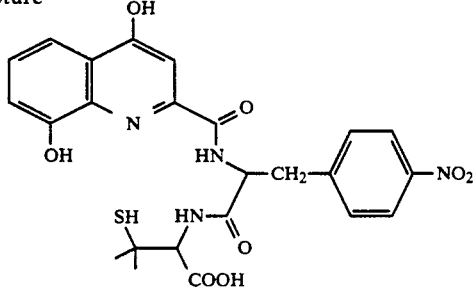

5. A compound of the claim 1 having the chemical structure

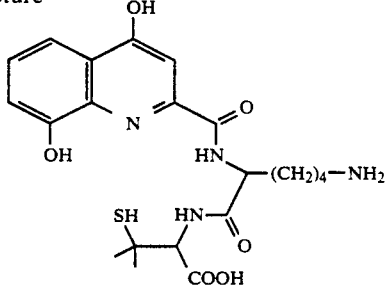

6. A compound of the compound of the claim 1 having the chemical structure

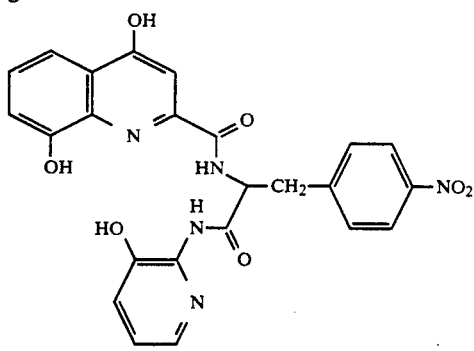

7. A compound of the claim 1 having the chemical structure

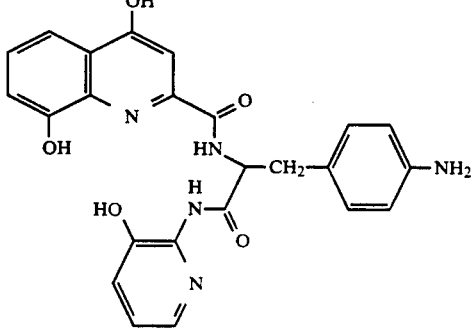

* * * * *